United States Patent
Terry et al.

(10) Patent No.: US 6,908,681 B2
(45) Date of Patent: Jun. 21, 2005

(54) SILANE COPOLYMER COATINGS

(75) Inventors: Richard N. Terry, Conyers, GA (US); Kevin Walsh, Atlanta, GA (US)

(73) Assignee: C.R. Bard, Inc., Murray Hill, NJ (US)

( * ) Notice: Subject to any disclaimer, the term of this patent is extended or adjusted under 35 U.S.C. 154(b) by 0 days.

(21) Appl. No.: 09/887,680

(22) Filed: Oct. 26, 2001

(65) Prior Publication Data

US 2002/0128419 A1 Sep. 12, 2002

Related U.S. Application Data

(63) Continuation of application No. 09/189,240, filed on Nov. 10, 1998, now Pat. No. 6,329,488.

(51) Int. Cl.$^7$ .......................... B32B 25/20; C08G 77/04
(52) U.S. Cl. ........................ 428/447; 427/2.28; 528/28; 528/29
(58) Field of Search .................. 428/447; 427/2.28; 528/28, 29

(56) References Cited

U.S. PATENT DOCUMENTS

| | | | |
|---|---|---|---|
| 3,522,142 A | 7/1970 | Wismer et al. | |
| 3,627,722 A | 12/1971 | Seiter | |
| 4,026,296 A | 5/1977 | Stoy et al. | |
| 4,100,309 A | 7/1978 | Micklus et al. | |
| 4,118,354 A | 10/1978 | Harada et al. | |
| 4,119,094 A | 10/1978 | Micklus et al. | |
| 4,373,009 A | 2/1983 | Winn | |
| 4,374,237 A | 2/1983 | Berger et al. | |
| 4,462,665 A | 7/1984 | Shah | |
| 4,487,808 A | 12/1984 | Lambert | |
| 4,539,345 A | 9/1985 | Hansen | |
| 4,582,873 A * | 4/1986 | Gaa et al. | 524/591 |
| 4,585,666 A | 4/1986 | Lambert | |
| 4,603,152 A | 7/1986 | Laurin et al. | |
| 4,612,337 A | 9/1986 | Fox, Jr. et al. | |
| 4,636,346 A | 1/1987 | Gold et al. | |
| 4,642,267 A | 2/1987 | Creasy et al. | |
| 4,645,816 A * | 2/1987 | Pohl et al. | 528/28 |
| 4,677,143 A | 6/1987 | Laurin et al. | |
| 4,798,878 A | 1/1989 | Brinkmann et al. | |
| 4,847,324 A | 7/1989 | Creasy | |
| 4,857,623 A | 8/1989 | Emmerling et al. | |
| 4,963,310 A | 10/1990 | Mitamura et al. | |
| 4,973,320 A | 11/1990 | Brenner et al. | |
| 4,990,357 A | 2/1991 | Karakelle et al. | |
| 5,001,009 A | 3/1991 | Whitbourne | |
| 5,026,607 A | 6/1991 | Kiezulas | |
| 5,041,100 A | 8/1991 | Rowland et al. | |
| 5,049,140 A | 9/1991 | Brenner et al. | |
| 5,061,424 A | 10/1991 | Karimi et al. | |
| 5,077,352 A | 12/1991 | Elton | |
| 5,084,315 A | 1/1992 | Karimi et al. | |
| 5,160,790 A | 11/1992 | Elton | |
| 5,179,174 A | 1/1993 | Elton | |
| 5,227,434 A | 7/1993 | Katz | |
| 5,290,548 A * | 3/1994 | Goldberg et al. | 424/78.18 |
| 5,290,585 A | 3/1994 | Elton | |
| 5,397,848 A | 3/1995 | Yang et al. | |
| 5,423,735 A | 6/1995 | Callinan et al. | |
| 5,429,839 A | 7/1995 | Graiver et al. | |
| 5,459,317 A | 10/1995 | Small et al. | |
| 5,492,951 A | 2/1996 | Beyrle et al. | |
| 5,509,899 A | 4/1996 | Fan et al. | |
| 5,554,686 A | 9/1996 | Frisch, Jr. et al. | |
| 5,554,709 A | 9/1996 | Emmerling et al. | |
| 5,558,900 A | 9/1996 | Fan et al. | |
| 5,576,072 A | 11/1996 | Hostettler et al. | |
| 5,614,604 A | 3/1997 | Krafcik | |
| 5,736,251 A * | 4/1998 | Pinchuk | 428/447 |
| 6,046,270 A * | 4/2000 | Roesler et al. | 524/590 |
| 6,329,488 B1 * | 12/2001 | Terry et al. | 528/28 |
| 6,384,171 B1 * | 5/2002 | Yamazaki et al. | 528/15 |
| 6,428,839 B1 * | 8/2002 | Kunzler et al. | 427/2.1 |

FOREIGN PATENT DOCUMENTS

| | | |
|---|---|---|
| AU | 27113/77 | 1/1979 |
| DE | 3629237 | 3/1988 |
| DE | 2738979 | 6/1989 |
| EP | 0170865 A1 | 12/1986 |
| EP | 0210444 A1 | 2/1987 |
| EP | 0261409 A1 | 8/1987 |
| EP | 0371370 A1 | 6/1990 |
| FR | 1140301 | 7/1957 |
| FR | 1189998 | 10/1959 |
| FR | 1217009 | 4/1960 |
| FR | 1254063 | 12/1961 |
| WO | WO 89/09246 | 10/1989 |

OTHER PUBLICATIONS

Abstract, Derwent Publications,Ltd., XP002137135 & JP 03 063061, (1991).

Nagoacha et al., *Biomaterials* 419 (1990).

* cited by examiner

*Primary Examiner*—Jeffrey B. Robertson
(74) *Attorney, Agent, or Firm*—Kilpatrick Stockton LLP

(57) ABSTRACT

The invention is drawn to silane copolymers prepared from the reaction of one or more polyisocyanates with one or more lubricious polymers having at least two functional groups, which may be the same or different, that are reactive with an isocyanate functional group and with one or more organo-functional silanes having at least two functional groups, which may be the same or different, that are reactive with an isocyanate functional group and at least one functional group reactive with a silicone rubber substrate. The silane copolymer coatings of the invention are elastic, lubricious, and resist wet abrasion. They are useful as coatings for polysiloxane (rubber) and other difficult to coat substrates, especially for medical devices, such catheters.

91 Claims, No Drawings

US 6,908,681 B2

SILANE COPOLYMER COATINGS

CLAIM OF PRIORITY

This application is a continuation of U.S. patent application Ser. No. 09/189,240, filed Nov. 10, 1998 now U.S. Pat. No. 6,329,488.

FIELD OF THE INVENTION

The invention relates generally to biocompatible, hydrophilic coatings, their manufacture, and their use for coating silicone and other difficult to coat medical devices. More specifically, the invention relates to hydrophilic coatings which are elastic when dry and resist wet abrasion, and to their use as coatings for polydimethylsiloxane (silicone) rubber substrates.

BACKGROUND OF THE INVENTION

In the practice of medicine there are many diagnostic and therapeutic procedures which require the insertion of a medical device into the human body through an orifice or tissue or contact of a medical device with blood or tissue. Such devices include guidewires; catheters, including Foley, angioplasty, diagnostic, and balloon catheters; implant devices; contact lenses; IUDs; peristaltic pump chambers; endotracheal tubes; gastroenteric feed tubes; arteriovenous shunts; condoms; and oxygenator and kidney membranes. It is necessary for the surface of these medical devices to have a low coefficient of friction to prevent injury, irritation, or inflammation to the patient and to facilitate medical and surgical procedures.

There is a need in the art for medical devices with the appropriate degree of slipperiness. The appropriate level is one at which the device is very slippery when contacted with the patient's moist tissue, but is not so slippery when dry that it is difficult for medical personnel to handle. Current materials from which such medical devices are made include silicone rubber, Teflon®, polyethylene (PE), polypropylene (PP), polyvinyl chloride (PVC), polyurethane (PU), polytetrafluoroethylene (PTFE), Nylon®, polyethylene terephthalate (PET), and glass. These materials, however, lack the desired degree of slipperiness.

One approach to providing medical devices with more desirable surface characteristics is to coat the devices made from existing materials with various coating compositions. These coatings may be applied by spraying or painting the coating on the device or by dipping the device in a solution of the coating. Some substances which have been employed as coatings are Teflon®, silicone fluid, glycerin, mineral oils, olive oil, K-Y jelly, and fluorocarbons. However, these substances have not been entirely satisfactory because they lack hydrophilicity, are not retained on the device surface during the period of use, are non-durable, or exhibit inadequate retention of lubricity.

Hydrophilic polymer and hydrogel coatings were an improvement to the art and have been used successfully to provide coatings for many of the easier to coat substrates, such as polyurethane and latex rubber. These coatings, however, are poorly adherent to silicone rubber and wash off when the device is wetted.

Many medical devices such as guidewires, catheters, implant devices, contact lenses, IUDs, peristaltic pump chambers, endotracheal tubes, gastroenteric feed tubes, artenovenous shunts, condoms, and oxygenator and kidney membranes are made from silicone rubber or other difficult to coat materials, such as Teflon®, polyethylene and polypropylene. Thus, there is a special need in the art for hydrophilic coatings for these and similarly difficult to coat substrates.

Adherence of previously known coatings to such surfaces is difficult because the coatings do not form covalent bonds with the silicone. As a result, the coatings have poor adherence, reduced durability, and poor resistance to wet abrasion.

Various polymers have been employed as coatings for medical devices. These include polyethylene oxide (PEO), polyethylene glycol (PEG), polyvinyl pyrrolidone (PVP), and polyurethane (PU). PEO and PEG are friction-reducing, blood-compatible polymers that are commercially available in a variety of molecular weights. Both have been used in combination with various other materials to produce lubricious coatings for medical devices. For example, coatings incorporating PEO and isocyanates are known in the art (U.S. Pat. Nos. 5,459,317, 4,487,808, and 4,585,666 to Lambert; and U.S. Pat. No. 5,558,900 to Fan et al.). In addition, polyols may be incorporated into such PEO/isocyanate coatings to produce a crosslinked polyurethane (PU) network entrapping the PEO (U.S. Pat. Nos. 5,077,352 and 5,179,174 to Elton). PEO has also been combined with structural plastic having a high molecular weight to produce a coating with reduced friction (U.S. Pat. No. 5,041,100 to Rowland).

None of these coatings are acceptable for coating silicone rubber and other difficult to coat substrates. Because these coatings do not form covalent linkages with the silicone surface of the substrate, they have poor adherence and durability and are easily washed from the surface when the substrate is wetted.

Another polymer used to coat medical devices is polyvinyl pyrrolidone (PVP). PVP may be used as a coating alone or in combination with other polymers. For example, polyvinyl pyrrolidone may be bonded to a substrate by thermally activated free radical initiators, UV light activated free-radical initiators, or E-beam radiation (WO 89/09246). One disadvantage of using such coatings is that E-beam radiation can be deleterious to some of the materials used in medical devices.

PVP may be used in conjunction with other polymers. One such coating is made from PVP and glycidyl acrylate. This coating requires the presence of amino groups on the surface of the substrate to react with the epoxy groups of the glycidyl acrylate to covalently bond the PVP-containing copolymer to the substrate (Nagoacha et al, *Biomaterials*, 419 (1990)). Silicone rubber does not contain any free amino groups, and thus this type of coating cannot form covalent bonds with the surface of the silicone substrate, resulting in poor adhesion.

Other coatings are composed of a mixture of PVP and polyurethane. These coatings provide low friction surfaces when wet. One such coating is a polyvinyl pyrrolidone-polyurethane interpolymer (U.S. Pat. Nos. 4,100,309 and 4,119,094 to Micklus et al.). Another such coating is composed of hydrophilic blends of polyvinyl pyrrolidone (PVP) and linear preformed polyurethanes (U.S. Pat. No. 4,642,267 to Cresy). In addition, PVP may be incorporated into a PU network by combining a polyisocyanate and a polyol with a PVP solution (U.S. Pat. Nos. 5,160,790 and 5,290,585 to Elton). Still another such coating is composed of two layers: a primer and a top coat. The primer coat is a polyurethane prepolymer containing free isocyanate groups, while the top coat is a hydrophilic copolymer of PVP and a polymer having active hydrogen groups, such as acrylamide (U.S. Pat. No. 4,373,009 to Winn).

None of these PVP based coatings are acceptable for coating silicone rubber and other difficult to coat substrates. Because these coatings do not form covalent linkages with the silicone surface of the substrate, they have poor adherence and durability and are easily washed from the surface when the substrate is wetted.

Hydrophilic polyurethanes have also been used in formulations other than with PVP as coatings for medical devices. For example, the prior art discloses coatings composed of polyurethane hydrogels containing a random mixture of polyisocyanates and a polyether dispersed in an aqueous liquid phase (U.S. Pat. No. 4,118,354 to Harada et al.). Polyurethanes have also been used as coatings in compositions containing chain-extended hydrophilic thermoplastic polyurethane polymers with a variety of hydrophilic high molecular weight non-urethane polymers (U.S. Pat. No. 4,990,357 to Karkelle et al.). It is also known to mix urethane with a silicone or siloxane emulsion. The carboxylic acid groups of the substrate and coating may then be linked with a cross-linking agent, such as a polyfunctional aziridine (U.S. Pat. No. 5,026,607 to Kiezulas).

Because the urethane and non-urethane polymers cannot react with one another or the surface to be coated, the resulting coatings have poor adhesion, especially to silicone surfaces. Also, since silicone surfaces do not contain free carboxylic acid groups, a crosslinker such as a polyfunctional aziridine will not covalently bond known coatings to the surface of a silicone substrate.

Thus, there is a critical need in the art for an improved coating which is not slippery when dry but becomes slippery when contacted with aqueous fluids and which will adhere to medical devices made from silicone and other difficult to coat materials.

There is also a need in the art for a coating having improved durability and uniformity which retains its lubricity and will adhere to medical devices made from silicone and other difficult to coat materials.

There is also a need in the art coatings which are biocompatible and abrasion resistant, having a low wet coefficient of friction, that will adhere to medical devices made from silicone and other difficult to coat materials.

There is a further need in the art for a process of preparing lubricious coatings for medical devices made from silicone and other difficult to coat materials which is simple and efficient and results in uniformity between batches.

SUMMARY OF THE INVENTION

Stated generally, the present invention comprises biocompatible, hydrophilic silane copolymers, their manufacture, and their use as coatings for polydimethylsiloxane rubber and other difficult to coat substrates. The coatings of the invention provide advantageous properties, such as improved durability, uniformity, and adhesion to silicone and other surfaces which are difficult to coat, such as polyethylene and polypropylene. The coatings of the present invention are beneficial because they retain lubricity and do not leach excessively over time.

Stated somewhat more specifically, the invention in a first aspect comprises a method for preparing a silane copolymer from one or more polyisocyanates, from one or more lubricious polymers having at least two functional groups, which may be the same or different, that are reactive with an isocyanate functional group, and from one or more organo-functional silanes having at least two functional groups, which may be the same or different, that are reactive with an isocyanate functional group and at least one functional group reactive with a silicone rubber substrate. The invention also comprsises the silane copolymers made from the process described above.

In another aspect, the present invention comprises using the silane copolymers described herein to coat polysiloxane rubber and other difficult to coat substrates. The coatings may comprise either a single layer or multiple layers. In one preferred embodiment, the copolymers of the invention are employed as a primer coat over which a top coat is applied. In s another preferred embodiment, the coating is applied as the sole coating to the catheter. In yet another preferred embodiment, the copolymer coating incorporates additional components, including other hydrophilic polymers. Also included in the invention are the coatings formed from the silane copolymers and the articles containing such coatings.

Thus, it is an object of the present invention to provide an improved coating for silicone and other difficult to coat substrates which is not slippery when dry but becomes slippery when contacted with aqueous fluids.

It is another object of the invention to provide a coating with improved durability and uniformity which retains its lubricity.

Further, it is an object of the present invention to provide a coating with improved adhesion to silicone and other surfaces that are difficult to coat.

Additionally, it is an object of the invention to provide a coating which does not leach over time.

It is an object of the invention to provide coatings which are biocompatible and abrasion resistant, having a low coefficient of friction.

It is another object of the present invention to provide a single layer, lubricious coating.

It is yet another object of the invention to provide a multi-layer coating which comprises a primer coating layer and a lubricious top coat.

It is an object of the invention to provide a polyurethane-silane copolymer.

It is another object of the present invention to provide a polyurethane-urea-silane copolymer.

It is a further object of the present invention to provide a process of preparing lubricious coatings which is simple and efficient and results in uniformity between batches.

DETAILED DESCRIPTION OF THE PREFERRED EMBODIMENTS

It should be understood to those well versed in the art of polymer and polyurethane synthesis that the copolymer coatings of the present invention may take many different forms and may be made by many different methods, and that the disclosure of the preferred embodiments herein do not limit the scope of the invention.

Preparing the Silane Copolymers of the Invention

Generally the present invention comprises a process for preparing silane copolymers. Stated somewhat more specifically, the invention in a first aspect comprises a method for preparing a silane copolymer from one or more polyisocyanates, from one or more lubricious polymers having at least two functional groups, which may be the same or different, that are reactive with an isocyanate functional group, and from one or more organo-functional silanes having at least two functional groups, which may be the same or different, that are reactive with an isocyanate functional group and at least one functional group reactive with a silicone rubber substrate.

The process of the invention may be performed in many variations. For example, the silane copolymers of the present invention can be prepared by first forming a prepolymer from the polyisocyanate(s) and lubricious polymer(s) followed by reaction with the organo-functional silane(s). Alternatively, the silane copolymers of the invention can be prepared by first forming a prepolymer from the polyisocyanate(s) and silane(s) followed by reaction with the lubricious polymer(s). Additionally, the silane copolymers of the invention can be prepared by simultaneously adding the polyisocyanate(s), lubricious polymer(s), and silane(s) and allowing them to react with one another to form the copolymer of the invention.

While any monomers satisfying the definition above may be employed in the invention, for convenience, the process of invention will be described further in terms of the production of polyurethane-urea-silane copolymers. However, it should be understood that these specific copolymers are only preferred embodiments and in no way limit the scope of the invention.

In one disclosed embodiment, one or more polyols are reacted with an excess of one or more polyisocyanates in the presence of a catalyst, such as a tin catalyst. The polyurethane product of this first step is then reacted with one or more amino-functional alkoxysilanes to form a polyurethane-urea-silane copolymer having pendant alkoxy groups. This polyurethane-urea-silane copolymer is then optionally stabilized in solution by the addition of an alcohol, preferably the alcohol formed by the reaction of the alkoxy group with water.

In a preferred form of the embodiment, one or more polyols are reacted with an excess of a diisocyanate in a first step to form an isocyanate-capped polyurethane prepolymer. The formation of this prepolymer can be facilitated by employing an excess of polyisocyanate. In other words, the number of isocyanate functional groups present in the reaction mixture is greater than the number of alcohol function groups present in the reaction mixture. Preferably, the ratio of isocyanate functional groups to alcohol or other isocyanate reactive functional groups is from 1.1:1 to 2:1. More preferably, the ratio of isocyanate functional groups to alcohol functional groups is from 1.5:1 to 2:1, most preferably 1.6 to 1.8.

The reaction between the polyol and polyisocyanate can also be facilitated by employing a catalyst. Nonlimiting examples of suitable catalysts are tertiary amines, such as N,N-dimethylaminoethanol N,N-dimethyl-cyclohexamine-bis(2-dimethyl aminoethyl) ether, N-ethylmorpholine, N,N, N',N',N"-pentamethyl-diethylene-triamine, and 1–2 (hydroxypropyl) imidazole, and metallic catalysts, such as tin, stannous octoate, dibutyl tin dilaurate, dioctyl tin dilaurate, dibutyl tin mercaptide, ferric acetylacetonate, lead octoate, and dibutyl tin diricinoleate. The preferred catalyst is tin. The most preferred catalyst is dioctyl tin dilaurate.

In a second step, the isocyanate-capped polyurethane-urea prepolymer is reacted with an organo-functional silane to form a polyurethane-urea-silane copolymer having pendant alkoxy groups. Any organo-functional silane having at least two functional groups, which may be the same or different, that are reactive with an isocyanate functional group, and at least one functional group reactive with a silicone surface may be used in the process of the present invention. The reaction can be facilitated by performing the polymerization in a dry organic solvent. If the silicone reactive group of the silane is alkoxy, an optional third step comprises stabilization of the alkoxy groups of the polyurethane-urea-silane copolymer by the addition an alcohol of the alcohol corresponding to the reaction product of the alkoxy group with water.

In a second disclosed embodiment, one or more amino-functional alkoxysilanes are reacted with an excess of one or more polyisocyanates, preferably a diisocyanate. The polyurea product of this first step is then combined with one or more polyols, optionally in the presence of a catalyst, such as a tin catalyst. If a catalyst is used, a polyurethane-urea-silane copolymer having pendant alkoxy groups. This polyurethane-urea-silane copolymer is then optionally stabilized in solution by addition of the alcohol corresponding to the alcohol formed by the reaction of the alkoxy group with water.

In a third disclosed embodiment of the process, one or more amino-functional alkoxysilanes are reacted with one or more polyisocyanates, preferably a diisocyanate, and one or more polyols, optionally in the presence of a catalyst, such as a tin catalyst, to form a polyurethane-urea-silane copolymer having pendant alkoxy groups. This polyurethane-urea-silane copolymer is then optionally stabilized in solution by addition of the alcohol corresponding to the alcohol formed by the reaction of the alkoxy group with water.

When alokysilanes are used in the present invention, the resulting polyurethane-urea-silane copolymers contain numerous free alkoxy groups which react with the silicone surface but can also react with any water present in the reaction system. The reaction of the alkoxy groups with water cleaves alcohol from the copolymer and leaves silanol groups in place of the alkoxy groups. These silanols may react with the silicone substrate or with each other, the latter producing crosslinks in the copolymer which can affect coating properties.

Addition to the copolymer solution of the alcohol formed by the reaction of the alkoxy group contained in the copolymer and water helps to stabilize the copolymer by inhibiting the reaction of alkoxy groups with water. Examples of such alcohols include, but are not limited to, methanol, ethanol, 1-propanol, 2-propanol, butanol, hexanol and octanol. The particular alcohol used will depend upon the alkyl portion of the alkoxy group. For example, methanol is used to stabilize a copolymer containing methoxy groups. The alcohol is generally added at the end of polymerization in an amount from 5 to 50% of the total solvent composition, preferably from 10 to 30%.

Any polyol may be used in the process of the invention and is preferably dried to less than 1000 ppm water before reaction. Examples of such polyols include, but are not limited to, polyethylene glycols, polyester polyols, polyether polyols, caster oil polyols, and polyacrylate polyols, including Desmophen A450, Desmophen A365, and Desmophen A160 (Mobay Corporation, Pittsburgh, Pa.).

The process advantageously employs a diol as the polyol. Suitable diols include, but are not limited to, poly(ethylene adipates), poly(diethyleneglycol adipates), polycaprolactone diols, polycaprolactone-polyadipate copolymer diols, poly (ethylene-terephthalate)diols, polycarbonate diols, polytetramethylene ether glycol, polyethylene glycol, ethylene oxide adducts of polyoxypropylene diols, ethylene oxide adducts of polyoxypropylene triols. The preferred polyol is the diol polyethylene glycol. The most preferred polyethylene glycol is CARBOWAX 1450 (available from Union Carbide).

Instead of polyols, amine functional polymers may be used in the process of the invention to produce isocyanate-functionalized polyureas for reaction with an amino-functional alkoxysilane. Additionally, amine functional chain extenders common to the art of polyurethane synthesis and water which also produces polyureas by reaction with isocyanates to produce amines, may also be employed. Monomers containing such chain extenders also produce polyureas. Replacement of polyols with other polymers having functional groups reactive with isocyanates, as well as the use of other common polyurethane/polyurea synthetic techniques known to the art are anticipated by the process of the present invention.

Any polyisocyanate may be used in the process of the present invention. The polyisocyanate may be aromatic, aliphatic or cycloaliphatic. Nonlimiting examples of such polyisocyanates are 4,4'-diphenylmethane diisocyanate and position isomers thereof, 2,4- and 2,6-toluene diisocyanate (TDI) and position isomers thereof, 3,4-dichlorophenyl diisocyanate, dicyclohexylmethane-4,4'-diisocyanate (HMDI), 4,4'-diphenylmethane diisocyanate (MDI), 1,6-hexamethylene diisocyanate (HDI) and position isomers thereof, isophorone diisocyanate (IPDI), and adducts of diisocyanates, such as the adduct of trimethylolpropane and diphenylmethane diisocyanate or toluene diisocyanate. The preferred polyisocyanate is the diisocyanate dicyclohexylmethane-4,4'-diisocyanate (HMDI).

Any organo-functional silanes having at least two functional groups, which may be the same or different, that are reactive with an isocyanate functional group and at least one functional group reactive with a silicone surface may be used in the process of the present invention. Nonlimiting examples of organo-functional silanes are N-beta-(aminoethyl)-gamma-aminopropyl-trimethoxy silane and N-(2-aminoethyl)-3-aminopropylmethyl-dimethoxy silane. The preferred organo-functional silane is a diamino-alkoxysilane, such as N-(2-aminoethyl)-3-aminopropylmethyldimethoxy silane.

In general, it is beneficial to add a catalyst to the isocyanate reaction mixtures. Although any catalyst known to be useful in isocyanate reactions may be employed, the preferred catalyst for the present invention is any tertiary amine or metallic catalyst. Nonlimiting examples of suitable catalysts include tertiary amines, such as N,N-dimethylaminoethanol, N,N-dimethyl-cyclohexamine-bis (2-dimethyl aminoethyl) ether, N-ethylmorpholine, N,N,N',N',N"-pentamethyl-diethylene-triamine, and 1-2 (hydroxypropyl) imidazole, and metallic catalysts, such as tin, stannous octoate, dibutyl tin dilaurate, dioctyl tin dilaurate, dibutyl tin mercaptide, ferric acetylacetonate, lead octoate, and dibutyl tin diricinoleate. The preferred catalyst is tin with the most preferred being dioctyl tin dilaurate.

A solvent is advantageously added to the prepolymer or monomer mixture to reduce viscosity. The level of viscosity is important during the synthesis of the copolymers of the present invention. During polymerization, if the copolymer solution attains too high a viscosity, the solution can form a gel from which good quality coatings cannot be made. Once the polymerization is complete, if the copolymer solution has too high a viscosity, the coating formed will be too thick to produce a uniform thin coating on the substrate. Such a coating may also have low durability due to cracking. On the other hand, if copolymer solution has too low a viscosity, the coating formed will exhibit poor and uneven adhesion.

Viscosity is a function of molecular weight of the copolymer and the solids content of the solution and is controlled by addition of solvent to the solution. The preferred copolymer solution for dip coating has a kinematic viscosity in a range of about 1.5 to 20 cS (centistokes), preferably 2.0 to 10 cS, and most preferably 2.5 to 5 cS. The preferred copolymer solution has a solids content in a range of about 0.4 to 5%, most preferably from 0.6 to 1.5%.

It is preferred but not essential that the solvent be dry to prevent water contamination of the prepolymer because water may react with alkoxy groups of the silane. The solvent preferably contains less than 200 ppm water. Solvents which are useful in the present invention include, but are not limited to, tetrahydrofuran, acetonitrile, ethyl acetate, methylene chloride, dibromomethane, chloroform, dichloroethane, and dichloroethylene, with tetrahydrofuran being preferred.

The Silane Copolymers of the Invention

In a second aspect, the present invention comprises the silane copolymers made by the processes described above. These copolymers are preferably polyurethane-urea-silane copolymers. Particularly preferred copolymers are polyurethane-urea-silane copolymers having from 7 to 12% by weight silane based upon the weight of the entire copolymer. The most preferred copolymers of the invention are those comprised of dicyclohexylmethane-4,4'-diisocyanate, N-(2-aminoethyl)-3-aminopropylmethyldimethoxy silane, and CARBOWAX 1450.

The silane copolymers can contain additional components. For example, they may contain viscosity and flow control agents, antioxidants, conventional pigments, air release agents or defoamers, and other hydrophilic polymers.

Antioxidants are not necessary, but may be used to improve the oxidative stability of the coatings. Nonlimiting examples of useful antioxidants are vitamin E, tris(3,5-di-t-butyl-4-hydroxy benzyl) isocyanurate, 2,2'-methylenebis (4-methyl-6-t-butyl phenol), 1,3,5-trimethyl-2,4,6-tris(3,5-di-t-butyl-4-hydroxy benzyl) benzene, butyl-hydroxytoluene, octadecyl-3,5-di-t-butyl-4-hydroxy hydrocinnamate, 4,4'-methylenebis(2,6-di-t-butylphenol), p,p'-dioctyl-diphenylamine, and 1,1,3-tris-(2-methyl-4-hydroxy-5-t-butylphenyl)butane.

Conventional dyes and pigments can be added to impart color or radiopacity or to enhance the aesthetic appearance of the coatings produced from the copolymers.

The Use of the Copolymers as Lubricious Coatings

In a third aspect, the present invention comprises a method for using the silane copolymers described above to form a lubricious coating on difficult to coat substrates. Although the preferred substrate is a polysiloxane rubber, the copolymer is also useful for coating other difficult to coat substrates, such as polyethylene and polypropylene, as well as other polymers, glass, metal, and ceramics. Many medical devices, such as guide wires; catheters, including Foley, angioplasty, diagnostic, and balloon catheters; implant devices; contact lenses; IUDs; peristaltic pump chambers; endotracheal tubes; gastroenteric feed tubes; arteriovenous shunts; condoms; and oxygenator and kidney membranes, are made from silicone rubber and these other substrates.

The silane copolymers of the invention may be applied to the substrate by conventional methods known in the art. In general, the substrate is dipped into a solution of the copolymer of the present invention. Preferably, the substrate is dipped into the copolymer solution at a rate of about 15–80 inches per minute (ipm), preferably about 40 ipm. The substrate is preferably allowed to remain in the coating solution for 0–30 seconds, preferably about 5–15 seconds, and then is withdrawn at a rate of about 10–80 ipm, preferably 15–30 ipm. Once the substrate has been coated with the copolymer of the invention, it is allowed to air dry for at least 1 hour. The substrate may optionally be dried with a hot air stream or in an oven at a temperature of approximately 50 to 100° C. for about 5–60 minutes to remove residual solvent.

The silane copolymers of the present invention can be used to form a variety of unique coatings by varying the exact components incorporated into the copolymer. Some of the copolymers are both very lubricious and adhesive to the substrate. These copolymers can be used as the sole coating on the substrate. Other of the copolymers of the invention are less lubricious but have superior adhesion. These copolymers can be used as a primer coat over which a lubricious top coat may be attached.

In a first disclosed embodiment, the silane copolymer of the invention may be applied to the substrate as a primer coat over which a second lubricious top coat is then applied. In this embodiment, the silane copolymer acts as a primer, facilitating adhesion of the second top coat to the substrate. The top coat may be applied by any method, but is advantageously applied by dipping the primed substrate into a solution of the top coat in a manner similar to that by which the primer is applied.

As mentioned above, the preferred polyol used in the preparation of the silane copolymer is polyethylene glycol (PEG). PEG is a polymeric diol which is available in a variety of molecular weights. The use of PEG having different molecular weights affects the molecular weight and lubricity of the coatings formed. When the silane copolymer is used as a primer coat, a PEG having a lower molecular weight, such as CARBOWAX_1450, is used. The use of CARBOWAX 1450 provides a prepolymer having a weight average molecular weight ($M_w$) that is generally between about 1,900 and 25,000 as measure by gel permeation chromatography (GPC). A copolymer made from such a prepolymer provides improved adhesion of the primer coat to the substrate.

The lubricious top coat may be any coating which enhances the lubricity of the substrate. One preferred top coat is the combination of a higher molecular weight polyethylene oxide, such as Hydroslide 121 (C.R. Bard, Inc., Murray Hill, N.J.) or a polyvinyl pyrrolidone and a reactive mixture of polyfunctional isocyanate and polyol. Examples of such top coats include the coatings disclosed in U.S. Pat. Nos. 5,077,352; 5,179,174; 5,160,790; and 5,209,585, herein incorporated by reference.

Alternatively, the lubricious top coat that is applied over the primer coat is the silane copolymer of the present invention made with a higher molecular weight PEG, such as CARBOWAX 8000. Copolymers made from a higher molecular weight PEG, such as CARBOWAX 8000, exhibit an increased lubricity over copolymers made with a lower molecular weight PEG such as that used in the primer coat.

In a second disclosed embodiment, the silane copolymers of the invention may be applied to the substrate as a single coating when a sufficiently lubricious polyol, such as CARBOWAX 8000, is incorporated into the copolymer. The copolymers of the invention may be used alone as the single coating, or may incorporate additional hydrophilic polymers into the copolymer to add desirable properties to the coating. The preferred copolymers of this embodiment contain at least one additional hydrophilic polymer, such as polyethylene glycol (PEG), polyethylene oxide (PEG), or polyvinyl pyrrolidone (PVP).

Hydrophilic polymers that may be added to the copolymer solution include, but are not limited to, polyethylene oxide (PEO), polyethylene glycol (PEG), polysaccharides, hyaluronic acid and its salts and derivatives, sodium alginate, chondroitin sulfate, celluloses, chitin, chitosan, agarose, xanthans, dermatan sulfate, keratin sulfate, emulsan, gellan, curdlan, amylose, carrageenans, amylopectin, dextrans, glycogen, starch, heparin sulfate, and limit dextrins and fragments thereof; synthetic hydrophilic polymers, poly (vinyl alcohol), and poly(N-vinyl) pyrrolidone (PVP). The preferred hydrophilic polymer for use in the present invention is polyethylene glycol.

Properties of Lubricious Coatings of the Invention

The lubricious coatings made by this process have a number of advantageous properties. These properties include a reduced coefficient of friction when wet, providing a very slippery surface, increased coating adhesion to silicone and other difficult to coat substrates, and increased coating durability on such substrates.

Coefficient of friction (COF) is a measure of how slippery the coating is when contacted with another surface, such as body tissue. The lower the COF, the more slippery is the coating. Medical devices whose surfaces become slippery when wet decrease patient discomfort and decrease trauma to the patient's tissue. It is, therefore, desirable to produce a coating having as low of a COF as possible when wet. The coatings of the present invention have a COF when wet of between 0.01 and 0.2, preferably between 0.01 and 0.12, and more preferably between 0.01 and 0.06. In contrast, uncoated surfaces of most medical devices typically have wet COFs greater than 0.35. Thus, coatings of the present invention are excellent for use on the surface of medical devices, especially those made of silicone and other difficult to coat surfaces because they reduce the COF of the surfaces.

Coating adhesion and durability are both affected by the copolymer's molecular weight. The molecular weight in turn is dependent upon a number of factors: (1) the amount of water initially present in the polyol, (2) the final prepolymer molecular weight, (3) the prepolymer isocyanate functionality, (4) how close the ratio of prepolymer isocyanate groups to amine groups in the organo-functional silane approaches a 1:1 stoichiometric ratio, (5) purity of the silane monomer, (6) the water content of the solvents used, and (7) the degree of viscosity the copolymer is allowed to attain before the final dilution.

An important factor which contributes to both the copolymer molecular weight and the reproducibility of the copolymer synthesis is water contamination. Water can affect the copolymer molecular weight and the reproducibility of the copolymer synthesis in several ways. First, because water reacts with isocyanate groups to form primary amines, it can affect the stoichiometry of the polymerization. Second, water can react with the methoxy groups of DAS to form crosslinks within the copolymer, which dramatically increase the molecular weight of the copolymer. Therefore, it is desirable to limit the amount of water present during manufacture of the coating. Some of the ways to limit water contamination are the use of molecular sieves, vacuum drying, anhydrous reactants and a dry, inert atmosphere. If polyethylene glycol or other hygroscopic starting material is used in the copolymer synthesis, it is preferred that it be adequately dried to a consistent moisture level before use. Hygroscopic materials such as polyethylene glycol can absorb significant quantities of water from the air in a short period of time.

The ratio of isocyanate groups on the prepolymer to amine groups on the organo-functional silane also affects the molecular weight of the copolymer. A 1:1 ratio produces a copolymer approaching infinite molecular weight. The number of free isocyanate groups present in the prepolymer limits the number of sites available for reaction with the amine groups on the organo-functional silane. Similarly, the purity of the silane affects the number of amine groups available for reaction.

This invention is further illustrated by the following examples, which are not to be construed in any way as imposing limitations upon the scope of the invention.

EXPERIMENTAL DATA

Example 1
Preparation of Polyethylene Glycol

To a glass jar was added 200 g of polyethylene glycol (PEG) 1450 (Union Carbide) followed by the addition of 50 g molecular sieves. The jar was then placed in a vacuum oven at 68° C. for 72 hours under full vacuum. The water content of the PEG was then analyzed by Karl Fischer titration and determined to be 454 ppm.

Example 2
Preparation of Urethane Prepolymer

A three neck 300 ml round bottom flask was equipped with an overhead stirrer, a nitrogen inlet, and a nitrogen bubbler. The flask was placed in a 70° C. oil bath. The nitrogen bubbler was removed and 11.60 g dried, molten PEG 1450 was injected into the flask with a syringe. To the molten PEG was added 4.03 g of Desmodur W (Bayer, Inc. Germany) by syringe. The flask was then flushed with nitrogen, and a nitrogen blanket was maintained over the reaction mixture throughout the procedure.

The reaction mixture was stirred until homogenous. Next, 0.015 g of dioctyl tin dilaurate was added to the reaction mixture with a syringe. The mixture was then stirred for 1.2 hours at 68° C. to form the urethane prepolymer.

Example 3
Synthesis of polurethane-urea-silane copolymer primer

A three-neck, 500 ml, round bottom flask was set up with an overhead stirrer, addition funnel with nitrogen inlet, and septum seal with nitrogen bubbler (outlet). The system was flushed with nitrogen. 111.5 g of dry (less than 100 ppm water) tetrahydrofuran (THF) was added to the urethane prepolymer prepared in Example 2, and the mixture was stirred until homogenous.

Next, 1.53 g of N-(2-aminoethyl)-3-aminopropyl-methyldimethoxy silane (DAS) (Gelest, Inc.) was dissolved in 38.63 g THF and added continuously to the prepolymer solution via the addition funnel over a period of approximately five minutes to begin the polymerization. The solids concentration of the solution was approximately 10% at this point.

The viscosity of the mixture was monitored, and when it increased to 70.9 centipoise (cP), 48.3 g of anhydrous THF was added. The viscosity fell and then began building again. When it reached 70.0 cP again, 49.33 g of anhydrous THF was added. This process was repeated, adding another 48.62 g of anhydrous THF when 67.6 cP was reached. When the viscosity reached the fourth target of 66.0 cP, 30.16 g of THF was added to produce a 5% solids solution. When the viscosity reached a final viscosity of 67.1 cP, the solution was transferred into a 2 L vessel containing 690 g of THF and stirred until homogeneous. 354.3 g of methanol was then added to stabilize the silane copolymer, producing a final solution concentration of 1.2% solids. The amount of methanol in the solvent mixture was sufficient to produce a final methanol concentration of 25% of the total solvent. The copolymer solution was then diluted to 0.81% solids with a solution of 75% THF and 25% methanol to produce a final viscosity of 4.02 cS.

Example 4
Preparation of Hydroslide 121 Polyurethane Hydrogel 3.42 g of Polyox N750 (Union Carbide) was dissolved in 580.6 g dichloromethane. 1.09 g Polycin 12 (Caschem, Inc.) was then added to the Polyox solution and stirred until homogenous. Then, 0.96 g Desmodur CB60N (Bayer, Inc., Germany) was added to the solution and mixed until homogenous.

Example 5

Thirty catheters were dipped into the primer copolymer solution of Example 3 at a rate of about 41.2 ipm. The catheters were allowed to remain in the coating solution for 10 seconds and then withdrawn at a rate of about 14.9 ipm. The catheters were air dried by passing a gentle stream of air through the drainage lumen of the catheters for about 5 minutes, followed by air drying for one hour.

Example 6

15 the thirty catheters from Example 5 were then dipped into a solution of the Hydroslide 121 coating prepared in Example 4 at a rate of 41.1 ipm and withdrawn at a rate of 15.2 ipm. The catheters were then air dried by passing a gentle stream of air through the drainage lumen for about 5 minutes, air drying them for an additional 30 minutes, and then placing them into an oven at 80° C. for 15 minutes. The catheters were allowed to cool and then packaged and sterilized with ethylene oxide (ETO). After sterilization, the coefficient of friction of 10 pairs of the silicone copolymer coated catheters was evaluated over a 21 day period in which the catheters were incubated in water at 37° C. When compared with the coefficient of friction of uncoated silicone catheters, the results confirmed a highly lubricious, durable hydrophilic coating on the silicone catheters.

| Coated? | 1 Day | 7 Day | 14 Day | 21 Day |
|---------|-------|-------|--------|--------|
| YES     | 0.023 | 0.026 | 0.032  | 0.048  |
| NO      | 0.216 | 0.237 | 0.160  | 0.183  |

Finally, it will be understood that the preferred embodiments have been disclosed by way of example, and that other modifications may occur to those skilled in the art without separating from the scope and spirit of the appended claims.

We claim:

1. An article comprising a polysiloxane rubber substrate having a surface coated with a coating wherein the coating comprises a copolymer that is the reaction product of molecules comprising:
   i) one or more molecules having at least two functional groups, which may be the same or different, that are reactive with isocyanate;
   ii) one or more organo-functional silanes having at least two functional groups that are reactive with an isocyanate group and at least one functional group reactive with a silicone rubber substrate; and,
   iii) one or more polyisocyanates.

2. The article of claim 1, wherein the article is a medical device.

3. The article of claim 1, wherein the article is a catheter.

4. An article according to claim 1, wherein the one or more organo-functional silanes comprise an amino-functional alkoxysilane.

5. The article of claim 4, wherein the amino-alkoxy silane is N-(2-aminoethyl)-3-aminopropyl-methyldimethoxy silane.

6. The article of claim 1, wherein the one or more molecules having at least two functional groups, which may be the same or different, that are reactive with isacyanates comprise a diol.

7. The article of claim 6, wherein the diol is a polyethylene adipate, a polydiethyleneglycol adipate, a polycaprolactone diol, a polycaprolactone-polyadipate copolymer diol, a polyethylene-terephthalate diol, a polycarbonate diol, a polytetramethylene ether glycol, a polyethylene glycol, an ethylene oxide adduct of a polyoxypropylene diol or an ethylene oxide adduct of a polyoxypropylene triol.

8. The article of claim 7, wherein the polyethylene glycol has a weight average molecular weight of about 1450.

9. The article of claim 7, wherein the polyethylene glycol has a weight average molecular weight of about 8000.

10. The article of claim 1, wherein the one or more polyisocyanates comprise a diisocyanate.

11. The article of claim 1, wherein the one or more polyisocyanates comprise 4,4'-diphenylmethane diisocyanate or a position isomer thereof, 2,4- or 2,6-toluene diisocyanate (TDI) or a position isomer thereof, 3,4-dichlorophenyl diisocyanate, dicyclohexylmethane-4,4'-diisocyanate (HMDI), 4,4'-diphenylmethane diisocyanate (MDI), 1,6-hexamethylene diisocyanate (HDI) or a position isomer thereof, isophorone diisocyanate (IPDI) or an adduct of a diisocyanate.

12. The article of to claim 10, wherein the diisocyanate is dicyclohexylmethane-4,4'-diisocyanate (HMDI).

13. The article of claim 1, wherein the silane copolymer is a polyurethane-urea-silane copolymer.

14. The article of claim 1, wherein 7–12% by weight of the copolymer is the silane based upon the weight of the entire copolymer.

15. The article of claim 1, wherein the coating further comprises a hydrophilic polymer.

16. The article of claim 15, wherein the hydrophilic polymer is a polysaccharide, hyaluronic acid or a salt or a derivative thereof, sodium alginate, chondroitin sulfate, a cellulose, chitin, chitosan, agarose, a xanthan, dermatan sulfate, keratin sulfate, emulsan, gellan, curdlan, amylose, carrageenan, amylopectin, a dextran, glycogen, starch, heparin sulfate, a limit dextrin or a fragment thereof or a synthetic hydrophilic polymer.

17. The article of claim 15, wherein the hydrophilic polymer is polyethylene oxide (PEO), polyethylene glycol (PEG), poly(vinyl alcohol) or poly(N-vinyl) pyrrolidone (PVP).

18. The article of claim 1, wherein the one or more polyisocyanates comprise dicyclohexylmethane-4,4'-diisocyanate (HMDI), the one or more organo-functional silanes comprise N-(2-aminoethyl)-3-aminopropyl-methyldimethoxy silane, and the molecules having at least two functional groups, which may be the same or different, that are reactive with isocyanate comprise a polyethylene glycol having a weight average molecular weight of about 1450.

19. The article of claim 1, wherein the coating comprises a primer coat and a top coat wherein:

the primer coat comprises the copolymer and the primer coat is located between the surface and the top coat.

20. The article of claim 19, wherein the top coat comprises polyethylene oxide and a reactive mixture of a polyfunctional isocyanate and a polyol.

21. The article of claim 19, wherein the top coat comprises polyvinyl pyrrolidone and a reactive mixture of a polyfunctional isocyanate and a polyol.

22. The article of claim 19, wherein the top coat is formed by reacting:

(i) one or more polyisocyanates, (ii) one or more organo-functional silanes having at least two functional groups, which may be the same or different and which are reactive with an isocyanate group, and at least one functional group reactive with a silicone rubber substrate, and (iii) a polyethylene glycol.

23. The article of claim 22, wherein the polyethylene glycol used to form the top coat has a weight average molecular weight of about 8000.

24. The article of claim 1, wherein the coating has a coefficient of friction when wet of between 0.01 and 0.2.

25. The article of claim 1, wherein the coating has a coefficient of friction when wet of between 0.01 and 0.12.

26. The article of claim 1, wherein the coating has a coefficient of friction when wet of between 0.01 and 0.06.

27. The article of claim 1, wherein the molecule having at least two functional groups, which may be the same or different, that are reactive with an isocyanate functional group, has at least two amino functional groups.

28. A silane copolymer that is the reaction product of molecules consisting essentially of:

i) a polymer having at least two functional groups, which may be the same or different, that are reactive with isocyanate;

ii) one or more organo-functional silanes having at least two functional groups that are reactive with an isocyanate group and at least one functional group that is reactive with a silicone rubber substrate; and, iii) one or more polyisocyanates.

29. The silane copolymer of claim 28, wherein the one or more organo-functional silanes comprise an amino-functional alkoxysilane.

30. The silane copolymer of claim 29, wherein the amino-alkoxy silane is N-(2-aminoethyl)-3-aminopropyl-methyldimethoxy silane.

31. The silane copolymer of claim 28, wherein the polymer having at least two functional groups, which may be the same or different, that are reactive with isocyanates is a diol.

32. The silane copolymer of claim 31, wherein the diol is a polyethylene adipate, a polydiethyleneglycol adipate, a polycaprolactone diol, a polycaprolactone-polyadipate copolymer diol, a polyethylene-terephthalate diol, a polycarbonate diol, a polytetramethylene ether glycol, a polyethylene glycol, an ethylene oxide adduct of a polyoxypropylene diol or an ethylene oxide adduct of a polyoxypropylene triol.

33. The silane copolymer of claim 31, wherein the diol is a polyethylene glycol.

34. The silane copolymer of claim 33, wherein the polyethylene glycol has a weight average molecular weight of about 1450.

35. The silane copolymer of claim 33, wherein the polyethylene glycol has a weight average molecular weight of about 8000.

36. The silane copolymer of claim 28, wherein the one or more polyisocyanates comprise a diisocyanate.

37. The silane copolymer of claim 28, wherein the one or more polyisocyanates comprise 4,4'-diphenylmethane diisocyanate or a position isomer thereof, 2,4- or 2,6-toluene diisocyanate (TDI) or a position isomer thereof, 3,4-dichlorophenyl diisocyanate, dicyclohexylmethane-4,4'-diisocyanate (HMDI), 4,4'-diphenylmethane diisocyanate (MDI), 1,6-hexamethylene diisocyanate (HDI) or a position isomer thereof, isophorone diisocyanate (IPDI) or an adduct of a diisocyanate.

38. The silane copolymer of claim 28, wherein the diisocyanate is dicyclohexylmethane-4,4'-diisocyanate (HMDI).

39. The silane copolyrner of claim 28, wherein the silane copolymer is a polyurethane-urea-silane copolymer.

40. The silane copolymer of claim 28, wherein 7–12% by weight of the copolymer is the silane based upon the weight of the entire copolymer.

41. The silane copolymer of claim 28, wherein the one or more polyisocyanates comprise dicyclohexylmethane-4,4'-diisocyanate (HMDI), the organo-functional silanes comprise N-(2-aminoethyl)-3-aminopropyl-methyldimethoxy silane, and the molecule having at least two functional groups, which may be the same or different, that are reactive with isocyanate is a polyethylene glycol having a weight average molecular weight of about 1450.

42. The silane copolymer of claim 28, wherein the polymer has a coefficient of friction when wet of between 0.01 and 0.2.

43. The silane copolymer of claim 28, wherein the polymer has a coefficient of friction when wet of between 0.01 and 0.12.

44. The silane copolymer of claim 28, wherein the polymer has a coefficient of friction when wet of between 0.01 and 0.06.

45. The silane copolymer of claim 28, wherein the molecule having at least two functional groups, which may be the same or different, that are reactive with an isocyanate functional group, has at least two amino functional groups.

46. A process comprising reacting molecules with each other to form a polymer, wherein the molecules consist essentially of:
  one or more polyisocyanates;
  a polymer having at least two functional groups, which may be the same or different, that are reactive with an isocyanate functional group; and,
  one or more organo-functional silanes having at least two functional groups, which may be the same or different, that are reactive with an isocyanate functional group, and having at least one functional group reactive with a silicone rubber substrate.

47. The process of claim 46, further comprising combining the molecules with a solvent.

48. The process of claim 46, further comprising the addition of a catalyst that is catalytic for the reaction between an isocyanate and a molecule having at least two functional groups, which may be the same or different, that are reactive with isocyanate.

49. The process of claim 46, wherein the catalyst is selected from the group consisting of N,N-dimethylaminoethanol, N,N-dimethyl-cyclohexamine-bis (2-dimethyl aminoethyl) ether, N-ethylmorpholine, N,N,N', N',N"-pentamethyl-diethylene-triamine, 1-2 (hydroxypropyl) imidazole, stannous octoate, dibutyl tin dilaurate, dioctyltin dilaurate, dibutyl tin mercaptide, ferric acetylacetonate, lead octoate, and dibutyl tin diricinoleate.

50. The process of claim 46, wherein the molecules having at least two functional groups, which may be the same or different, that are reactive with an isocyanate functional group comprise a diol.

51. The process of claim 46, wherein the molecules having at least two functional groups, which may be the same or different, that are reactive with isocyanate is a poly(ethylene adipate), a poly(diethyleneglycol adipate), a polycaprolactone diol, a polycaprolactone-polyadipate copolymer diol, a poly(ethylene-terephthalate)diol, a polycarbonate diol, a polytetramethylene ether glycol, a polyethylene glycol, an ethylene oxide adduct of polyoxypropylene diol, or an ethylene oxide adduct of polyoxypropylene triol.

52. The process of claim 50, wherein the diol is a polyethylene glycol.

53. The process of claim 52, wherein the polyethylene glycol has a weight average molecular weight of approximately 1450.

54. The process of claim 52, wherein the polyethylene glycol has a weight average molecular weight of approximately 8000.

55. The process of claim 46, wherein the one or more polyisocyanates comprise a diisocyanate.

56. The process of claim 55, wherein the diisocyanate is selected from 4,4'-diphenylmethane diisocyanate and position isomers thereof, 2,4- and 2,6-toluene diisocyanate (TDI) and position isomers thereof, 3,4-dichlorophenyl diisocyanate, dicyclohexylmethane-4,4'-diisocyanate (HMDI), 4,4'-diphenylmethane diisocyanate (MDI), 1,6-hexamethylene diisocyanate (HDI) and position isomers thereof, isophorone diisocyanate (IPDI), and adducts of diisocyanates.

57. The process of claim 55, wherein the diisocyanate is dicyclohexylmethane-4,4'-diisocyanate (HMDI).

58. The process of claim 46, wherein the one or more organo-functional silanes comprise an amino-functional alkoxysilane.

59. The process of claim 58, wherein the amino-functional alkoxysilane is N-(2-aminoethyl)-3-aminopropyl-methyldimethoxy silane.

60. The process of claim 46, wherein the molecule having at least two functional groups, which may be the same or different, that are reactive with an isocyanate functional group has at least two amine functional groups.

61. The process of claim 46, wherein reacting molecules with each other to form a polymer comprises:
  (a) reacting the molecules having at least two functional groups, which may be the same or different, that are reactive with isocyanate with an excess of the one or more polyisocyanates in the presence of a catalyst to form a polyurethane-urea prepolymer having terminal isocyanate groups; and
  (b) reacting the prepolymer formed in (a) with one or more organo-functional silanes having at least two functional groups, which may be the same or different, that are reactive with the isocyanate groups on the polyurethane-urea prepolymer and having at least one functional group reactive with a silicone rubber substrate to form a silane copolymer.

62. The process of claim 61 wherein (b) occurs in the presence of a solvent.

63. The process of claim 46, wherein reacting molecules with each other to form a polymer comprises:
  (a) reacting the one or more organo-functional silanes having at least two functional groups, which may be the same or different, that are reactive with an isocyanate functional group and having at least one functional group reactive with a silicone rubber substrate with an excess of the one or more polyisocyanates to form a polyurea prepolymer having terminal isocyanate groups; and, (b) reacting the polyurea prepolymer formed in (a) with the one or more molecules having at least two functional groups, which may be the same or different, that are reactive with isocyanate in the presence of a catalyst to form the silane copolymer.

64. The process of claim 63, wherein step (a) occurs in the presence of a solvent.

65. The process of claim 61, wherein the process further comprises stabilizing the copolymer formed in (b) by treating the copolymer with an alcohol.

66. The process of claim 63, wherein the process further comprises stabilizing the copolymer formed in (b) by treating the copolymer with an alcohol.

67. A coating comprising a silane copolymer wherein the copolymer is the reaction product of:

i) one or more molecules having at least two functional groups, which may be the same or different, that are reactive with isocyanate;

ii) one or more organo-functional silanes having at least two functional groups that are reactive with an isocyanate group and at least one functional group reactive with a silicone rubber substrate; and, iii) one or more polyisocyanates.

68. The coating of claim 67, wherein the coating comprises:

a primer coat comprising the silane copolymer; and, a top coat that overlays at least a portion of the primer coat.

69. The coating of claim 68, wherein the top coat is the combination of a polyethylene oxide and a reactive mixture of polyfunctional isocyanate and polyol.

70. The coating of claim 68, wherein the top coat is the reaction product of molecules comprising:

one or more polyisocyanates;

one or more organo-functional silanes having at least two functional groups, which may be the same or different, that are reactive with isocyanate and at least one functional group reactive with a silicone rubber substrate; and one or more polyethylene glycols.

71. The coating of claim 67, wherein the coating has a coefficient of friction when wet of between 0.01 and 0.2.

72. The coating of claim 67, wherein the coating has a coefficient of friction when wet of between 0.01 and 0.12.

73. The coating of claim 67, wherein the coating has a coefficient of friction when wet of between 0.01 and 0.06.

74. The coating of claim 67, wherein the molecule having at least two functional groups, which may be the same or different, that are reactive with an isocyanate functional group, has at least two amino functional groups.

75. The coating of claim 67, wherein the molecules having at least two functional groups, which may be the same or different, that are reactive with an isocyanate functional group comprise a diol.

76. The coating of claim 67, wherein the molecules having at least two functional groups, which may be the same or different, that are reactive with isocyanate are selected from a poly(ethylene adipate), a poly(diethyleneglycol adipate), a polycaprolactone diol, a polycaprolactone-polyadipate copolymer diol, a poly(ethylene-terephthalate)diol, a polycarbonate diol, a polytetramethylene ether glycol, a polyethylene glycol, an ethylene oxide adduct of polyoxypropylene diol, or an ethylene oxide adduct of polyoxypropylene triol.

77. The coating of claim 75, wherein the diol is a polyethylene glycol.

78. The coating of claim 77, wherein the polyethylene glycol has a weight average molecular weight of approximately 1450.

79. The coating of claim 77, wherein the polyethylene glycol has a weight average molecular weight of approximately 8000.

80. The coating of claim 67, wherein the one or more polyisocyanates comprise a diisocyanate.

81. The coating of claim 80, wherein the diisocyanate is selected from 4,4'-diphenylmethane diisocyanate and position isomers thereof, 2,4- and 2,6-toluene diisocyanate (TDI) and position isomers thereof, 3,4-dichlorophenyl diisocyanate, dicyclohexylmethane-4,4'-diisocyanate (HMDI), 4,4'-diphenylmethane diisocyanate (MDI), 1,6-hexamethylene diisocyanate (HDI) and position isomers thereof, isophorone diisocyanate (IPDI), and adducts of diisocyanates.

82. The coating of claim 80, wherein the diisocyanate is dicyclohexylmethane-4,4'-diisocyanate (HMDI).

83. The coating of claim 67, wherein the one or more organo-functional silanes comprise an amino-functional alkoxysilane.

84. The coating of claim 83, wherein the amino-functional alkoxysilane is N-(2-aminoethyl)-3-aminopropyl-methyldimethoxy silane.

85. The coating of claim 67, wherein the one or more polyisocyanates comprise dicyclohexylmethane-4,4'-diisocyanate (HMDI), the organo-functional silanes comprise N-(2-aminoethyl)-3-aminopropyl-methyldimethoxy silane, and the molecules having at least two functional groups, which may be the same or different, that are reactive with isocyanate is a polyethylene glycol having a weight average molecular weight of approximately 1450.

86. The coating of claim 67, wherein the molecule having at least two functional groups, which may be the same or different, that are reactive with an isocyanate functional group has at least two amine functional groups.

87. The coating of claim 67, wherein the coating further comprises a hydrophilic polymer.

88. The coating of claim 87, wherein the hydrophilic polymer is a polysaccharide, hyaluronic acid or a salt or a derivative thereof, sodium alginate, chondroitin sulfate, a cellulose, chitin, chitosan, agarose, a xanthan, dermatan sulfate, keratin sulfate, emulsan, gellan, curdlan, amylose, carrageenan, amylopectin, a dextran, glycogen, starch, heparin sulfate, a limit dextrin or a fragment thereof or a synthetic hydrophilic polymer.

89. The coating of claim 87, wherein the hydrophilic polymer is polyethylene oxide (PEO), polyethylene glycol (PEG), poly(vinyl alcohol) or poly(N-vinyl) pyrrolidone (PVP).

90. The coating of claim 68, wherein the top coat comprises polyvinyl pyrrolidone and a reactive mixture of a polyfunctional isocyanate and a polyol.

91. The coating of claim 70, wherein the polyethylene glycol used to form the top coat has a weight average molecular weight of about 8000.

* * * * *